(12) United States Patent
Buzby

(10) Patent No.: US 7,767,805 B2
(45) Date of Patent: Aug. 3, 2010

(54) METHODS AND COMPOSITIONS FOR SEQUENCING A NUCLEIC ACID

(75) Inventor: Philip Richard Buzby, Brockton, MA (US)

(73) Assignee: Helicos Biosciences Corporation, Cambridge, MA (US)

( * ) Notice: Subject to any disclaimer, the term of this patent is extended or adjusted under 35 U.S.C. 154(b) by 0 days.

(21) Appl. No.: 12/114,163

(22) Filed: May 2, 2008

(65) Prior Publication Data

US 2009/0061439 A1   Mar. 5, 2009

Related U.S. Application Data

(60) Provisional application No. 60/927,467, filed on May 3, 2007.

(51) Int. Cl.
| C07H 21/02 | (2006.01) |
| C07H 21/03 | (2006.01) |
| C07H 19/04 | (2006.01) |
| C12Q 1/68 | (2006.01) |
| C12P 19/34 | (2006.01) |
| C07H 21/00 | (2006.01) |

(52) U.S. Cl. .................. 536/26.6; 536/23.1; 536/24.3; 536/24.33; 536/25.3; 435/6; 435/91.1; 435/91.2

(58) Field of Classification Search ............ 536/23.1, 536/24.3, 24.33, 25.3, 26.6; 435/6, 91.1, 435/91.2

See application file for complete search history.

(56) References Cited

U.S. PATENT DOCUMENTS

| 6,072,043 A * | 6/2000 | Nilsen .................. 536/22.1 |
| 6,716,394 B2 | 4/2004 | Jensen et al. |
| 2005/0227231 A1 | 10/2005 | Tcherkassov |

OTHER PUBLICATIONS

International Search Report and Written Opinion of The International Searching Authority (Aug. 4, 2008) from the corresponding PCT application PCT/US08/62397 (7 pages).

Seo et al.; "Photocleavable Fluorescent Nucleotides for DNA Sequencing on a Chip Constructed by Site-Specific Coupling Chemistry"; Proc. Natl. Acad. Sci.; 101:5488-5493; Abstract; p. 5488, para 2; p. 5491, para 1; USA (2004).

Geoghegan et al.; "Dye-Pair Reporter Systems for Protein-Peptide Molecular Interactions"; Bioconjugate Chem; 11:71-77; Abstract (2000).

Randolph et al.; "Stability, Specificity and Fluorescence Brightness of Multiply-Labeled Fluorescent DNA Probes"; Nucleic Acids Research; 25:2923-2929; p. 2924, para 1 (1997).

International Preliminary Report on Patentability issued Nov. 12, 2009 in the corresponding PCT application PCT/US2008/062397 (6 pages).

* cited by examiner

*Primary Examiner*—Jezia Riley
(74) *Attorney, Agent, or Firm*—Thomas Meyers; Adam Schoen; Brown Rudnick LLP

(57) ABSTRACT

The invention provides nucleotide analogs and methods of using them in sequencing reactions.

17 Claims, 2 Drawing Sheets

METHODS AND COMPOSITIONS FOR SEQUENCING A NUCLEIC ACID

PRIORITY

This application claims benefit to U.S. Application Ser. No. 60/927,467, filed on May 3, 2007, the entire content of which is incorporated herein by reference

FIELD OF THE INVENTION

The invention relates to nucleotide analogs and methods for sequencing a nucleic acid using the nucleotide analogs.

BACKGROUND

Nucleic acid sequencing-by-synthesis has the potential to revolutionize the understanding of biological structure and function. Traditional sequencing technologies rely on amplification of sample-based nucleic acids and/or the use of electrophoretic gels in order to obtain sequence information. More recently, single molecule sequencing has been proposed as a way to obtain high-throughput sequence information that is not subject to amplification bias. See, Braslavsky, et al., *Proc. Natl. Acad. Sci.* USA 100: 3960-64 (2003).

Sequencing-by-synthesis involves the template-dependent addition of nucleotides to a support-bound template/primer duplex. Nucleotides are added to the 3' end of the primer portion of the duplex by a polymerase. In some cases, the added nucleotides are labeled in a manner such that their incorporation into the primer can be detected. A problem that is encountered when labeled nucleotides are used is that the labels are sometimes undetectable. For example, when fluorescent labels are used they can inadvertently be bleached by exposure to radiation (e.g., light). Also, if labels are reversibly-linked to the nucleotides they can prematurely be cleaved. If the label is prematurely inactivated or removed, incorporation of the affected nucleotide in the sequencing reaction may not be detectable. This results in errors in sequence determination due to these "missing bases" not being detected (i.e., nucleotides that do incorporate but are not detected and recorded due to problems with label detection). The problem of inadvertent label deactivation is a particular problem when optically-detectable labels, such as fluorophores, are used. Fluorophores can be deactivated by bleaching, precleavage (chemical removal prior to a detection step), or by steric inactivation. The present invention solves the problem of undetectable nucleotides in a sequencing-by-synthesis reaction.

SUMMARY OF THE INVENTION

The invention provides nucleotide analogs that comprise multiple labels of the same or different type in order to maximize the likelihood that the analogs will be detected upon incorporation in a sequencing-by-synthesis reaction. Analogs of the invention solve the problem of missing bases due to undetectable labels by including multiple labels on a nucleotide to be incorporated in a sequencing reaction. In this way, if one or more of the labels becomes inactivated or cleaved prematurely, the others will remain detectable and proper incorporation will be observable.

According to the invention, a nucleotide is linked to multiple labels via molecular linkers that vary depending upon the properties of the label. For example, if fluorescent labels are used, the fluors must be spaced so as to avoid quenching, but only to the extent that all of the fluors are quenched. In keeping with the principals of the invention, the use of multiple fluors contemplates that a subset of them may become quenched or otherwise inactivated, but as long as at least one fluor remains active, the nucleotide will be detectable upon incorporation. According to the invention, optically-detectable labels generally are preferred. Specific types are exemplified below. However, the invention contemplates any type of label (radiation, calorimetric, etc.) based upon the principal that if more labels are included, there is built-in compensation for prematurely deactivation of one or more of them (as long as at least one remains active).

Analogs of the invention are especially useful in single molecule nucleic acid sequence. In single molecule methods, template/primer duplex are attached to a surface such that they are individually optically resolvable. The template, the primer, or both may be attached to the surface. Optically-labeled nucleotides are then introduced in the presence of a polymerase for template-dependent incorporation (i.e., a nucleotide is incorporated at the 3' end of the primer if the adjacent base in the template is complementary). Incorporated nucleotides are detected based upon the presence of optically-detectable label at a position on the sequencing surface known to contain a duplex (as previously determined). Typically, there is a rinsing step prior to detection in order to wash away unbound nucleotides. Alternatively, a polymerase enzyme may be adhered to a surface and used to "anchor" the sequencing reaction. As labeled nucleotides are flowed past the polymerase, they are captured and incorporated in a template-dependent manner.

In one aspect, the invention provides a family of nucleotide analogs, each comprising a sugar portion, a nitrogenous base portion, a phosphate portion, and one or more linkers attached to one or more detectable labels. In a preferred embodiment, an analog of the invention comprises a nucleoside triphosphate linked to a detectable label via the C5 or C7 position on the base portion of the nucleotide to an alkyl, alkenyl, or aryl linker. Alternatively, labels are linked via the O6, N6, or O4 position of the base. Finally, labels can be linked via the 3' hydroxyl of the sugar portion or via the phosphates (at any of the available positions). Preferably, the multiple labels are linked via separate branch points off the linker. Also, separate labels can be linked via separate positions on the sugar, phosphate, or base portion of the nucleotide.

Linkers can be of any suitable molecular structure. Some preferred linkers include alkynyl, alkenyl, aryl, peptides, sugars, carbohydrates, carbamates, ethers, esters, phosphates, combinations of the foregoing, and any other suitable linkers known to the skilled artisan. A tether or linker is from about 4 to about 50 atoms in length. Preferably the linker comprises a lipophilic portion. The linker can also comprise a triple bond or a trans double bond proximal to the base to be incorporated. Finally, the linker contains a cleavable linkage that allows removal of the blocking portion of the molecule. The linker preferably should have a cleavable portion such that all of the labels can be removed after incorporation and detection. Removal may be accomplished by chemical means by photolysis, or by physical means. In one preferred embodiment, labels are linked via a multi-label peptide arm as shown below:

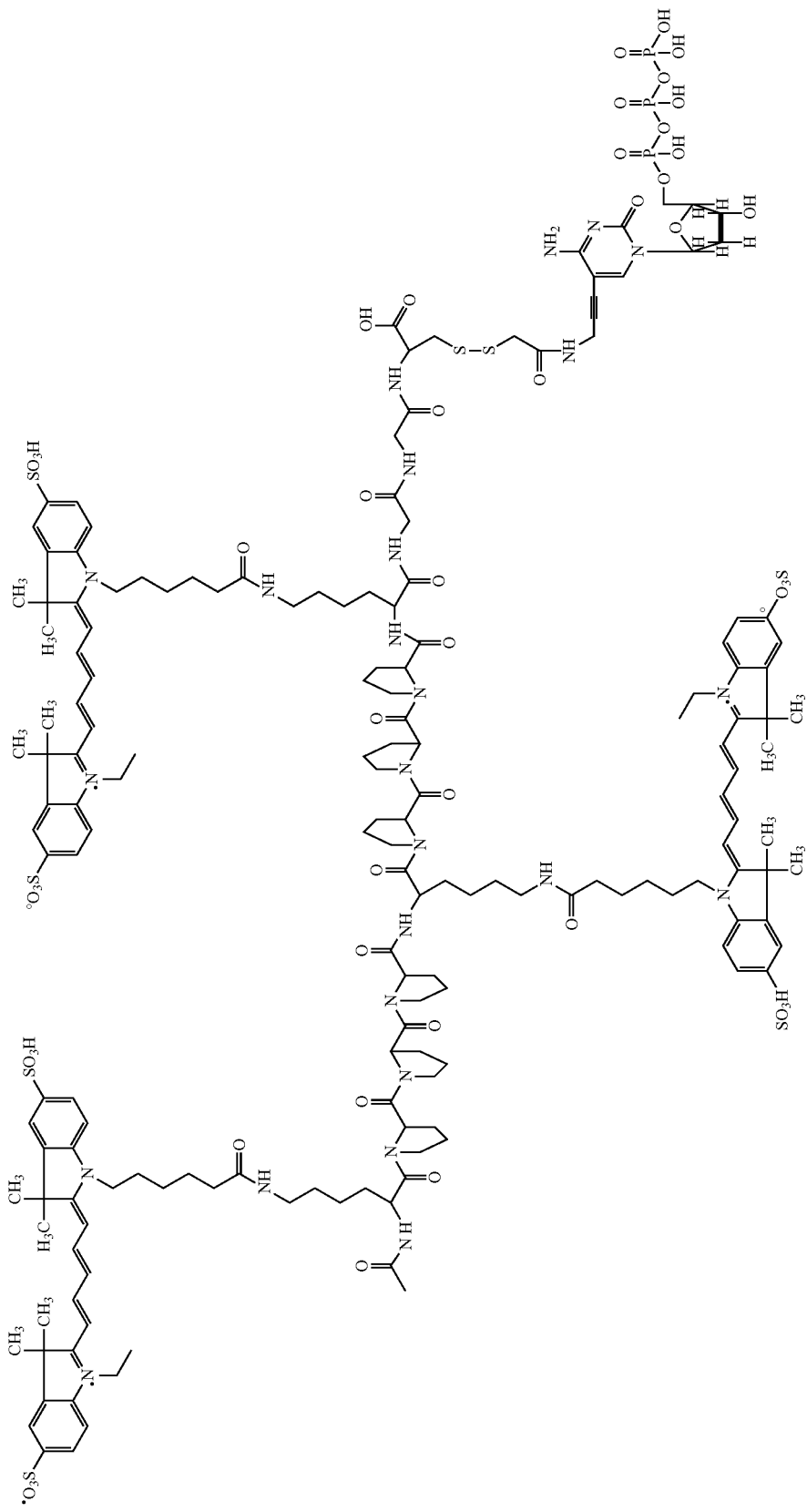

In another aspect, the invention provides a method for using the nucleotide analogs disclosed herein. The method includes imaging a nucleotide analog in the presence of a substance that is capable of disrupting dye:dye interactions thereby resulting in reduced or minimized dye quenching. In some embodiments, a water miscible organic solvent is present in an imaging solution used for imaging the nucleotide analog. Examples of organic solvents include alcohols, e.g., methanol or ethanol, or acetonitrile.

In general, a nucleotide analog of the invention comprises multiple labels attached in a manner that does not inhibit incorporation in a sequencing reaction and that preserves at least one detectable label in the sequencing reaction. For purposes of the invention, it doesn't matter if all of the labels are active, as long as at least one is active.

In a specific embodiment, the invention provides a nucleotide analog comprising a nucleotide to be incorporated linked to a blocker or inhibitor molecule in addition to the multiple labels. The inhibitor may be any molecule that does not interfere with incorporation of the nucleotide to which it is attached but that inhibits subsequent incorporation. In one example, the inhibitor may be a blocking nucleotide comprising a traditional Watson-Crick base (adenine, guanosine, cytosine, thymidine, or uridine), a sugar for example, a ribose or deoxy ribose sugar, and at least one phosphate. Examples of blockers or inhibitors may be found in U.S. Ser. No. 12/098,196 and PCT/US08/59446 (both filed on Apr. 4, 2008) and patents and patent applications referenced therein.

The invention also provides methods for sequencing nucleic acids. In certain methods, a nucleic acid duplex, comprising a template and a primer, is positioned on a surface such that the duplex is individually optically resolvable. A sequencing-by-synthesis reaction is performed under conditions to permit addition of a multiply-labeled nucleotide analog to the primer. After incorporation has been detected, inhibition is removed to permit another nucleotide to be added to the primer. Specific structures and synthetic pathways are shown below in the detailed description of the invention.

In certain embodiments, the invention provides a method for sequencing a nucleic acid. The method includes: anchoring a nucleic acid duplex to a surface, the duplex comprising a template portion and a primer portion hybridized thereto; exposing the duplex to nucleotide analogs disclosed herein in the presence of a polymerized capable of catalyzing the addition of the nucleotide analog to the primer portion in a template-dependent manner; removing unincorporated nucleotide analog and polymerase; detecting incorporation of the nucleotide analog into the primer portion; and repeating said exposing, removing, and detecting steps at least once.

BRIEF DESCRIPTION OF THE DRAWINGS

The invention may be further understood from the following figures in which.

DETAILED DESCRIPTION OF THE INVENTION

Figure 1A:
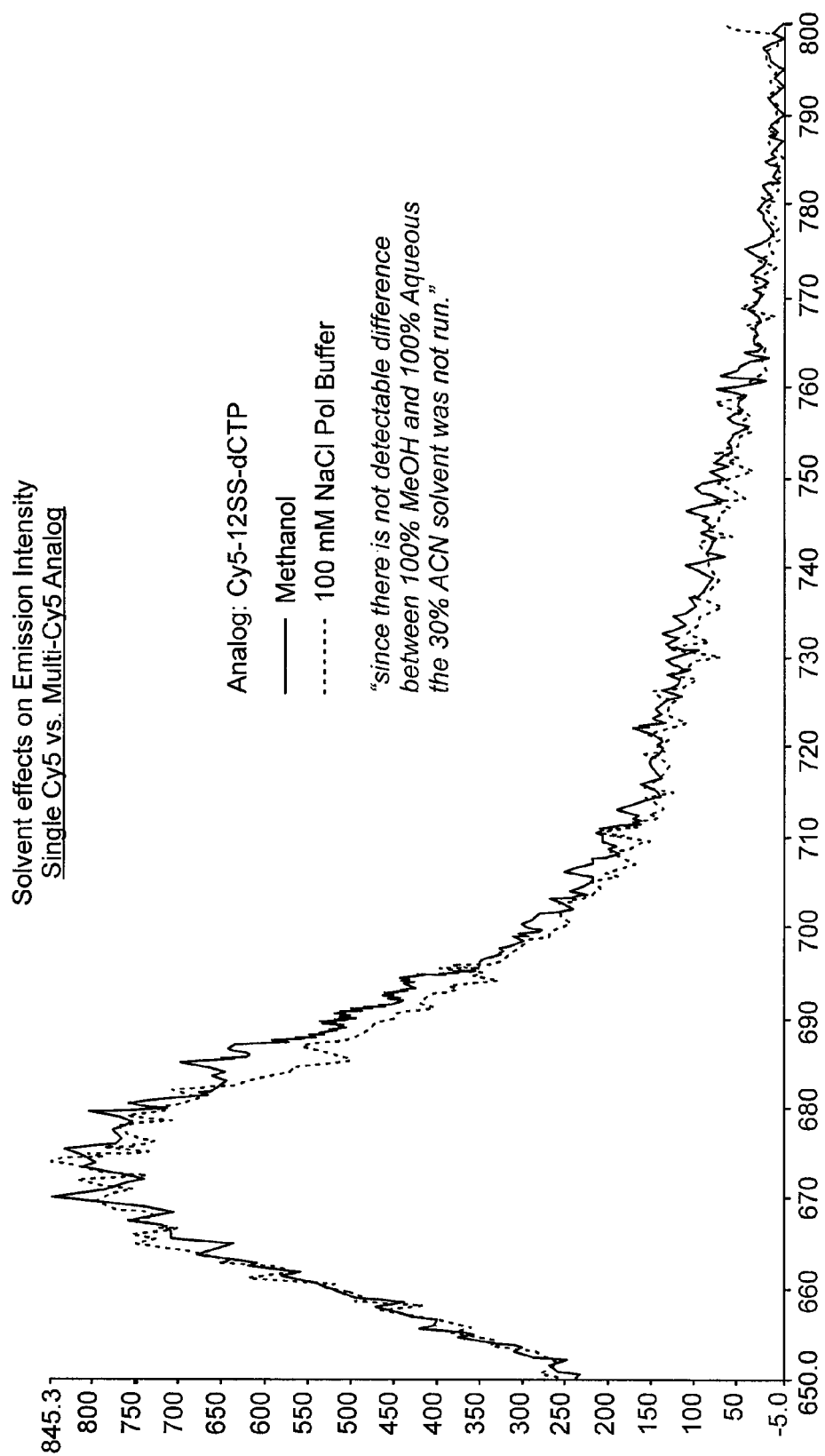
FIG. 1 shows exemplary spectral data on nucleotide analogs of the invention.

The invention provides nucleotide analogs and methods for their use in nucleic acid sequencing. Analogs of the invention comprise multiple labels as a mechanism to avoid a failure to detect a properly incorporated nucleotide in a sequencing reaction due to a premature inactivation or removal of the label.

Preferred analogs of the invention comprise a nucleotide or nucleotide analog to be incorporated linked to multiple labels, either via a straight chain linkage or a branch chain linkage. Analogs of the invention may optionally contain a blocker may be a bulky steric inhibitor or an unincorporated nucleotide or nucleotide analog linked via a cleavable linker containing, for example, a lipophilic or hydrophilic region to promote single incorporations and prevent homopolymer run-through. Specific examples of these analogs are provided below for illustrative purpose and in order to demonstrate methods of synthesis. However, the skilled artisan will appreciate that numerous variations are possible, consistent with the scope of the appended claims.

I. Nucleotide Analogs

Analogs preferably contain a nucleoside triphosphate attached to one or more linker(s) that, in turn, terminate in one or more labels. The precise structure of the linker and the label is of no moment to the operation of the invention, as the principle is that the analogs have more than one dye attached in a manner that does not inhibit incorporation of the nucleotide in a sequencing reaction (but that may inhibit subsequent incorporation prior to removal) and such that the labels are removable upon incorporation and detection.

Nucleotide analogs described herein permit template-dependent incorporation in a nucleic acid sequencing reaction. The term base pair encompasses not only the standard AT, AU or GC base pairs, but also base pairs formed between nucleotides and/or nucleotide analogs comprising non-standard or modified bases, wherein the arrangement of hydrogen bond donors and hydrogen bond acceptors permits hydrogen bonding between a non-standard base and a standard base or between two complementary non-standard base structures. One example of such non-standard base pairing is the base pairing between the nucleotide analog inosine and adenine, cytosine or uracil.

A generic analog of the invention is shown below:

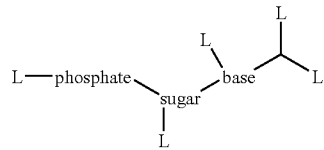

Wherein L is a label. The structure depicted above shows various attachment points for the label. Label can be attached at any of these or in any combination of them or can be solely the branched label structure shown as long as more than one label is attached. The labels may be the same or they may be of different types.

Certain additional generic embodiments are shown below. These are intended to be exemplary of the types of structures contemplated by the invention and are not intended to be limiting but to exemplify certain generic embodiments.

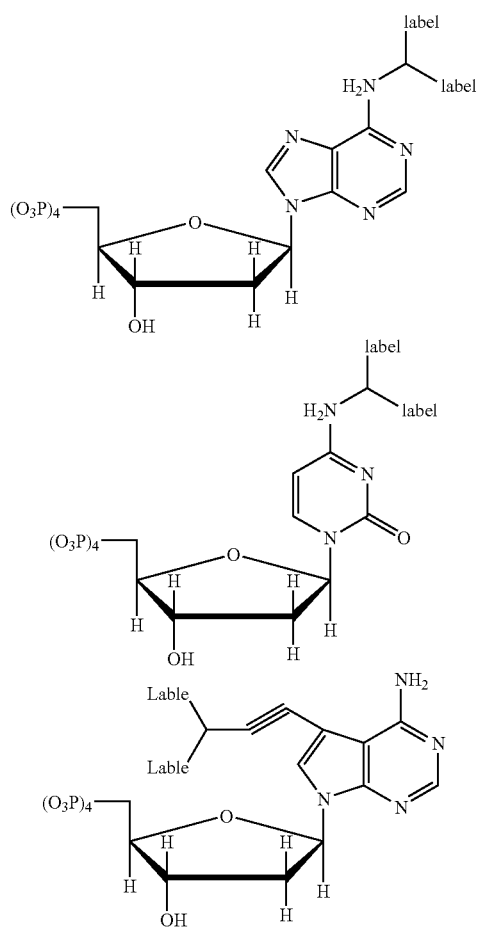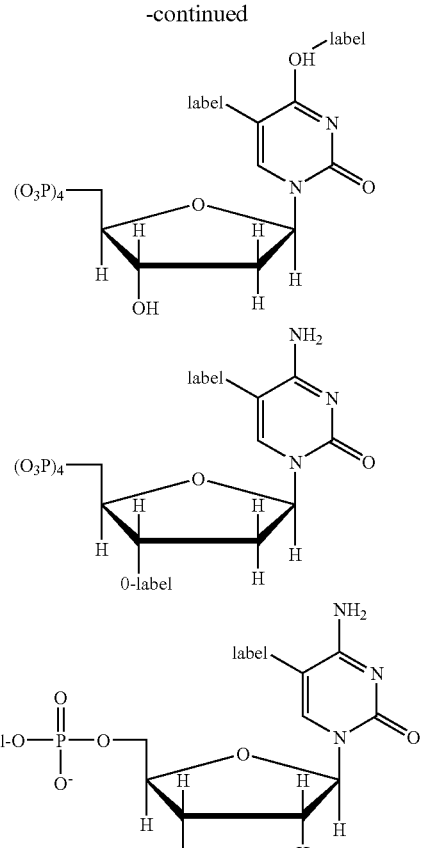
-continued
Another exemplary analog of the invention is shown below:

Compound 1
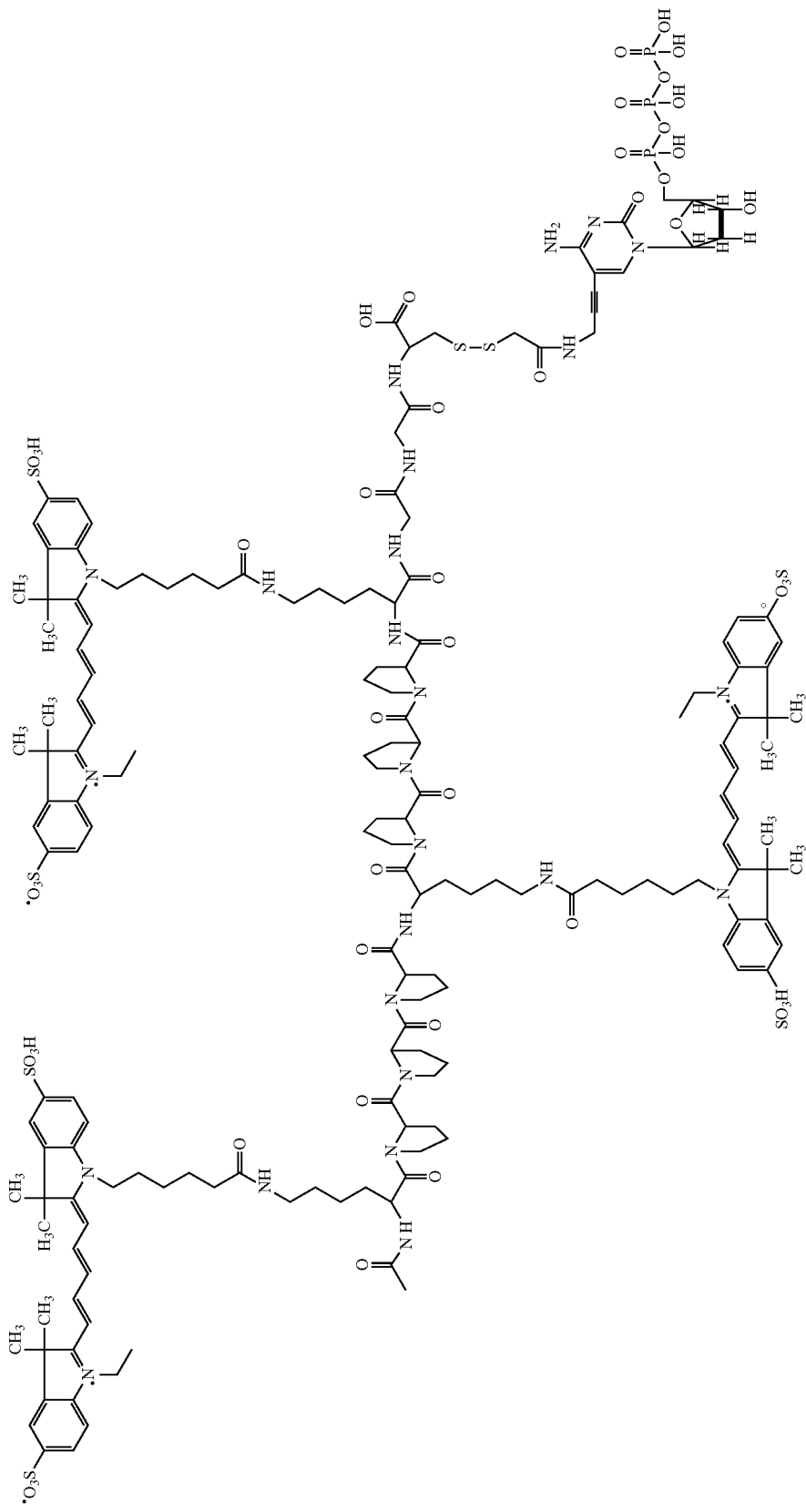

Another exemplary analog of the invention is shown below:

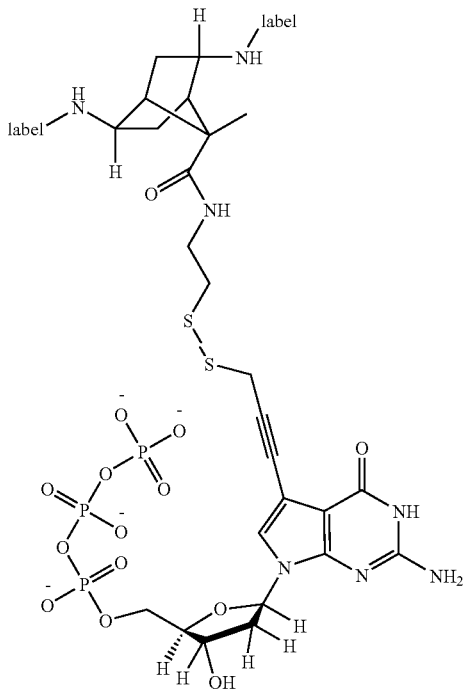

Labels used in analogs of the invention can be any suitable label. A preferred label is an optically-detectable label. A variety of optical labels can be used in the practice of the invention and include, for example, 4-acetamido-4'-isothiocyanatostilbene-2,2'disulfonic acid; acridine and derivatives: acridine, acridine isothiocyanate; 5-(2'-aminoethyl)aminonaphthalene-1-sulfonic acid (EDANS); 4-amino-N-[3-vinylsulfonyl)phenyl]naphthalimide-3,5 disulfonate; N-(4-anilino-1-naphthyl)maleimide; anthranilamide; BODIPY; Brilliant Yellow; coumarin and derivatives; coumarin, 7-amino-4-methylcoumarin (AMC, Coumarin 120), 7-amino-4-trifluoromethylcouluarin (Coumaran 151); cyanine dyes; cyanosine; 4',6-diaminidino-2-phenylindole (DAPI); 5'5"-dibromopyrogallol-sulfonaphthalein (Bromopyrogallol Red); 7-diethylamino-3-(4'-isothiocyanatophenyl)-4-methylcoumarin; diethylenetriamine pentaacetate; 4,4'-diisothiocyanatodihydro-stilbene-2,2'-disulfonic acid; 4,4'-diisothiocyanatostilbene-2,2'-disulfonic acid; 5-[dimethylamino]naphthalene-1-sulfonyl chloride (DNS, dansylchloride); 4-dimethylaminophenylazophenyl-4'-isothiocyanate (DABITC); eosin and derivatives; eosin, eosin isothiocyanate, erythrosin and derivatives; erythrosin B, erythrosin, isothiocyanate; ethidium; fluorescein and derivatives; 5-carboxyfluorescein (FAM), 5-(4,6-dichlorotriazin-2-yl)aminofluorescein (DTAF), 2',7'-dimethoxy-4'5'-dichloro-6-carboxyfluorescein, fluorescein, fluorescein isothiocyanate, QFITC, (XRITC); fluorescamine; IR144; IR1446; Malachite Green isothiocyanate; 4-methylumbelliferoneortho cresolphthalein; nitrotyrosine; pararosaniline; Phenol Red; B-phycoerythrin; o-phthaldialdehyde; pyrene and derivatives: pyrene, pyrene butyrate, succinimidyl 1-pyrene; butyrate quantum dots; Reactive Red 4 (Ciba-cron™ Brilliant Red 3B-A) rhodamine and derivatives: 6-carboxy-X-rhodamine (ROX), 6-carboxyrhodamine (R6G), lissamine rhodamine B sulfonyl chloride rhodamine (Rhod), rhodamine B, rhodamine 123, rhodamine X isothiocyanate, sulforhodamine B, sulforhodamine 101, sulfonyl chloride derivative of sulforhodamine 101 (Texas Red); N,N,N', N'tetramethyl-6-carboxyrhodamine (TAMRA); tetramethyl rhodamine; tetramethyl rhodamine isothiocyanate (TRITC); riboflavin; rosolic acid; terbium chelate derivatives; Cyanine-3 (Cy3); Cyanine-5 (Cy5); Cyanine-5.5 (Cy5.5), Cyanine-7 (Cy7); IRD 700; IRD 800; La Jolta Blue; phthalo cyanine; and naphthalo cyanine; any of the fluorescent labels available from Atto-Tec, for example, Atto 390, Atto 425, Atto 465, Atto 488, Atto 495, Atto 520, Atto 532, Atto 550, Atto 565, Atto 590, Atto 594, Atto 610, Atto 611X, Atto 620, Atto 633, Atto 635, Atto 637, Atto 647, Atto 647N, Atto 655, Atto 680, Atto 700, Atto 725, Atto 740.

Preferred labels are fluorescent dyes, such as Cy5 and Cy3. Labels other than fluorescent labels are contemplated by the invention, including other optically-detectable labels. Labels can be attached to the nucleotide analogs of the invention at any position using standard chemistries such that the label can be removed from the incorporated base upon cleavage of the cleavable linker.

II. Template-Directed Sequencing by Synthesis

The invention also generally relates to a method for sequencing a nucleic acid template includes exposing a nucleic acid template to a primer capable of hybridizing to the template and a polymerase capable of catalyzing nucleotide addition to the primer. The polymerase is, for example, Klenow with reduced exonuclease activity. The polymerase adds a labeled nucleotide analog disclosed herein. The method may include identifying the incorporated labeled nucleotide. Once the labeled nucleotide is identified, the label and at least a portion of a molecular chain connecting the label to the nucleotide analog are removed and the remaining portion of the molecular chain includes a free hydroxyl group. The exposing, incorporating, identifying, and removing steps are repeated at least once, preferably multiple times. The sequence of the template is determined based upon the order of incorporation of the labeled nucleotides.

Removal of a label from a disclosed labeled nucleotide analog and/or cleavage of the molecular chain linking a disclosed nucleotide to a label may include contacting or exposing the labeled nucleotide with a reducing agent. Such reducing agents include, for example, dithiothreitol (DTT), tris(2-carboxyethyl)phosphine (TCEP), tris(3-hydroxy-propyl) phosphine, tris(2-chloropropyl)phosphate (TCPP), 2-mercaptoethanol, 2-mercaptoethylamine, cystein and ethylmaleimide. Such contacting or exposing the reducing agent to a labeled nucleotide analog may occur at a range of pH values, for example at a pH of from about 5 to about 10, or from about 7 to about 9.

In one embodiment, the invention provides improved methods for sequencing a nucleic acid containing a homopolymer region. The method comprises exposing a nucleic acid template/primer duplex to (i) a polymerase that catalyzes nucleotide addition to the primer, and (ii) a labeled nucleotide analog comprising a nucleotide analog linked to multiple fluorophores under conditions that permit the polymerase to add the labeled nucleotide analog to the primer at a position complementary to the first base in the template. After the exposing step, the nucleotide analog incorporated into the primer is detected. Labels are removed by cleavage after detection. Then, the incorporation and detection steps are repeated. In certain embodiments, the nucleotide to be incorporated is also linked to a blocker that permits incorporation of only one nucleotide per incorporation cycle. The blocker, which may be one of the labels, is used to allow incorporation of nucleotides one at a time. This allows one to determine the number of nucleotides present in a homopolymer region of a template which, without the blocker, would be difficult due to the processivity of the polymerase in adding multiples of the same nucleotide per cycle. It is contemplated that the label can be removed at the same time as the blocker after incorporation and detection.

The following sections discuss general considerations for nucleic acid sequencing, for example, template considerations, polymerases useful in sequencing-by-synthesis, choice of surfaces, reaction conditions, signal detection and analysis.

Nucleic Acid Templates

Nucleic acid templates include deoxyribonucleic acid (DNA) and/or ribonucleic acid (RNA) and cDNA copies of RNA. Nucleic acid templates can be synthetic or derived from naturally occurring sources. In one embodiment, nucleic acid template molecules are isolated from a biological sample containing a variety of other components, such as proteins, lipids and non-template nucleic acids. Nucleic acid template molecules are obtained from any cellular material, obtained from an animal, plant, bacterium, fungus, or any other cellular organism. Biological samples for use in the present invention include viral particles or preparations. Nucleic acid template molecules can be obtained directly from an organism or from a biological sample obtained from an organism, e.g., from blood, urine, cerebrospinal fluid, seminal fluid, saliva, sputum, stool and tissue. Any tissue or body fluid specimen may be used as a source for nucleic acid for use in the invention. Nucleic acid template molecules can also be isolated from cultured cells, such as a primary cell culture or a cell line. The cells or tissues from which template nucleic acids are obtained can be infected with a virus or other intracellular pathogen. A sample can also be total RNA extracted from a biological specimen, a cDNA library, viral, or genomic DNA.

Nucleic acid obtained from biological samples typically is fragmented to produce suitable fragments for analysis. In one embodiment, nucleic acid from a biological sample is fragmented by sonication. Nucleic acid template molecules can be obtained as described in U.S. Patent Application Publication Number US2002/0190663 A1, published Oct. 9, 2003. Generally, nucleic acid can be extracted from a biological sample by a variety of techniques such as those described by Maniatis, et al., Molecular Cloning: A Laboratory Manual, Cold Spring Harbor, N.Y., pp. 280-281 (1982). Generally, individual nucleic acid template molecules can be from about 5 bases to about 20 kb. Nucleic acid molecules may be single-stranded, double-stranded, or double-stranded with single-stranded regions (for example, stem- and loop-structures).

A biological sample as described herein may be homogenized or fractionated in the presence of a detergent or surfactant. The concentration of the detergent in the buffer may be about 0.05% to about 10.0%. The concentration of the detergent can be up to an amount where the detergent remains soluble in the solution. In a preferred embodiment, the concentration of the detergent is between 0.1% to about 2%. The detergent, particularly a mild one that is nondenaturing, can act to solubilize the sample. Detergents may be ionic or nonionic. Examples of nonionic detergents include triton, such as the Triton® X series (Triton® X-100 t-Oct-$C_6H_4$—($OCH_2$—$CH_2$)$_x$OH, x=9-10, Triton® X-100R, Triton® X-114 x=7-8), octyl glucoside, polyoxyethylene(9)dodecyl ether, digitonin, IGEPAL® CA630 octylphenyl polyethylene glycol, n-octyl-beta-D-glucopyranoside (betaOG), n-dodecyl-beta, Tween® 20 polyethylene glycol sorbitan monolaurate, Tween® 80 polyethylene glycol sorbitan monooleate, polidocanol, n-dodecyl beta-D-maltoside (DDM), NP-40 nonylphenyl polyethylene glycol, C12E8 (octaethylene glycol n-dodecyl monoether), hexaethyleneglycol mono-n-tetradecyl ether (C14EO6), octyl-beta-thioglucopyranoside (octyl thioglucoside, OTG), Emulgen, and polyoxyethylene 10 lauryl ether (C12E10). Examples of ionic detergents (anionic or cationic) include deoxycholate, sodium dodecyl sulfate (SDS), N-lauroylsarcosine, and cetyltrimethylammoniumbromide (CTAB). A zwitterionic reagent may also be used in the purification schemes of the present invention, such as Chaps, zwitterion 3-14, and 3-[(3-cholamidopropyl)dimethylammonio]-1-propanesulf-onate. It is contemplated also that urea may be added with or without another detergent or surfactant.

Lysis or homogenization solutions may further contain other agents, such as reducing agents. Examples of such reducing agents include dithiothreitol (DTT), β-mercaptoethanol, DTE, GSH, cysteine, cysteamine, tricarboxyethyl phosphine (TCEP), or salts of sulfurous acid.

Nucleic Acid Polymerases

Nucleic acid polymerases generally useful in the invention include DNA polymerases, RNA polymerases, reverse transcriptases, and mutant or altered forms of any of the foregoing. DNA polymerases and their properties are described in detail in, among other places, DNA Replication 2nd edition, Kornberg and Baker, W. H. Freeman, New York, N.Y. (1991). Known conventional DNA polymerases useful in the invention include, but are not limited to, *Pyrococcus furiosus* (Pfu) DNA polymerase (Lundberg et al., 1991, Gene, 108: 1, Stratagene), *Pyrococcus woesei* (Pwo) DNA polymerase (Hinnisdaels et al., 1996, Biotechniques, 20:186-8, Boehringer Mannheim), *Thermus thermophilus* (Tth) DNA polymerase (Myers and Gelfand 1991, Biochemistry 30:7661), *Bacillus stearothermophilus* DNA polymerase (Stenesh and McGowan, 1977, Biochim Biophys Acta 475:32), *Thermococcus litoralis* (Tli) DNA polymerase (also referred to as Vent™ DNA polymerase, Cariello et al., 1991, Polynucleotides Res, 19: 4193, New England Biolabs), 9° Nm™ DNA polymerase (New England Biolabs), Stoffel fragment, ThermoSequenase™ (Amersham Pharmacia Biotech UK), Therminator™ (New England Biolabs), *Thermotoga maritima* (Tma) DNA polymerase (Diaz and Sabino, 1998 Braz J Med. Res, 31:1239), *Thermus aquaticus* (Taq) DNA polymerase (Chien et al., 1976, J. Bacteoriol, 127: 1550), DNA polymerase, *Pyrococcus kodakaraensis* KOD DNA polymerase (Takagi et al., 1997, Appl. Environ. Microbiol. 63:4504), JDF-3 DNA polymerase (from *thermococcus* sp. JDF-3, Patent application WO 0132887), *Pyrococcus* GB-D (PGB-D) DNA polymerase (also referred as Deep Vent™ DNA polymerase, Juncosa-Ginesta et al., 1994, Biotechniques, 16:820, New England Biolabs), UlTma DNA polymerase (from thermophile *Thermotoga maritima*; Diaz and Sabino, 1998 Braz J. Med. Res, 31:1239; PE Applied Biosystems), Tgo DNA polymerase (from *thermococcus gorgonarius*, Roche Molecular Biochemicals), *E. coli* DNA polymerase I (Lecomte and Doubleday, 1983, Polynucleotides Res. 11:7505), T7 DNA polymerase (Nordstrom et al., 1981, J. Biol. Chem. 256:3112), and archaeal DP1I/DP2 DNA polymerase II (Cann et al., 1998, Proc. Natl. Acad. Sci. USA 95:14250).

Both mesophilic polymerases and thermophilic polymerases are contemplated. Thermophilic DNA polymerases include, but are not limited to, ThermoSequenase® 9° Nm™, Therminator™, Taq, Tne, Tma, Pfu, Tfl, Tth, Tli, Stoffel fragment, Vent™ and Deep Vent™ DNA polymerase, KOD DNA polymerase, Tgo, JDF-3, and mutants, variants and derivatives thereof. A highly-preferred form of any polymerase is a 3' exonuclease-deficient mutant.

Reverse transcriptases useful in the invention include, but are not limited to, reverse transcriptases from HIV, HTLV-1, HTLV-II, FeLV, FIV, SIV, AMV, MMTV, MoMuLV and other retroviruses (see Levin, Cell 88:5-8 (1997); Verma, Biochim Biophys Acta. 473:1-38 (1977); Wu et al., CRC Crit Rev Biochem. 3:289-347 (1975)).

Surfaces

In a preferred embodiment, nucleic acid template molecules are attached to a substrate (also referred to herein as a surface) and subjected to analysis by single molecule sequencing as described herein. Nucleic acid template molecules are attached to the surface directly or indirectly such that the template/primer duplexes are individually optically resolvable. Substrates for use in the invention can be two- or three-dimensional and can comprise a planar surface (e.g., a glass slide) or can be shaped. A substrate can include glass (e.g., controlled pore glass (CPG)), quartz, plastic (such as polystyrene (low cross-linked and high cross-linked polystyrene), polycarbonate, polypropylene and poly(methymethacrylate)), acrylic copolymer, polyamide, silicon, metal (e.g., alkanethiolate-derivatized gold), cellulose, nylon, latex, dextran, gel matrix (e.g., silica gel), polyacrolein, or composites.

Suitable three-dimensional substrates include, for example, spheres, microparticles, beads, membranes, slides, plates, micromachined chips, tubes (e.g., capillary tubes), microwells, microfluidic devices, channels, filters, or any other structure suitable for anchoring a nucleic acid. Substrates can include planar arrays or matrices capable of having regions that include populations of template nucleic acids or primers. Examples include nucleoside-derivatized CPG and polystyrene slides; derivatized magnetic slides; polystyrene grafted with polyethylene glycol, and the like.

Substrates are preferably coated to allow optimum optical processing and nucleic acid attachment. Substrates for use in the invention can also be treated to reduce background. Exemplary coatings include epoxides, and derivatized epoxides (e.g., with a binding molecule, such as an oligonucleotide or streptavidin).

Various methods can be used to anchor or immobilize the nucleic acid molecule to the surface of the substrate. The immobilization can be achieved through direct or indirect (e.g., by a polymerase enzyme) bonding to the surface. The bonding can be by covalent linkage. See, Joos et al., Analytical Biochemistry 247:96-101, 1997; Oroskar et al., *Clin. Chem.* 42:1547-1555, 1996; and Khandjian, *Mol. Bio. Rep.* 11:107-115, 1986. A preferred attachment is direct amine bonding of a terminal nucleotide of the template or the 5' end of the primer to an epoxide integrated on the surface. The bonding also can be through non-covalent linkage. For example, biotin-streptavidin (Taylor et al., *J. Phys. D. Appl. Phys.* 24:1443, 1991) and digoxigenin with anti-digoxigenin (Smith et al., *Science* 253:1122, 1992) are common tools for anchoring nucleic acids to surfaces and parallels. Alternatively, the attachment can be achieved by anchoring a hydrophobic chain into a lipid monolayer or bilayer. Other methods for known in the art for attaching nucleic acid molecules to substrates also can be used.

Detection

Any detection method can be used that is suitable for the type of label employed. Thus, exemplary detection methods include radioactive detection, optical absorbance detection, e.g., UV-visible absorbance detection, optical emission detection, e.g., fluorescence or chemiluminescence. For example, extended primers can be detected on a substrate by scanning all or portions of each substrate simultaneously or serially, depending on the scanning method used. For fluorescence labeling, selected regions on a substrate may be serially scanned one-by-one or row-by-row using a fluorescence microscope apparatus, such as described in Fodor (U.S. Pat. No. 5,445,934) and Mathies et al. (U.S. Pat. No. 5,091,652). Devices capable of sensing fluorescence from a single molecule include scanning tunneling microscope (siM) and the atomic force microscope (AFM). Hybridization patterns may also be scanned using a CCD camera (e.g., Model TE/CCD512SF, Princeton Instruments, Trenton, N.J.) with suitable optics (Ploem, in Fluorescent and Luminescent Probes for Biological Activity Mason, T. G. Ed., Academic Press, Landon, pp. 1-11 (1993), such as described in Yershov et al., Proc. Natl. Acad. Sci. 93:4913 (1996), or may be imaged by TV monitoring. For radioactive signals, a phosphorimager device can be used (Johnston et al., Electrophoresis, 13:566, 1990; Drmanac et al., Electrophoresis, 13:566, 1992; 1993). Other commercial suppliers of imaging instruments include General Scanning Inc., (Watertown, Mass. on the World Wide Web at genscan.com), Genix Technologies (Waterloo, Ontario, Canada; on the World Wide Web at confocal.com), and Applied Precision Inc. Such detection methods are particularly useful to achieve simultaneous scanning of multiple attached template nucleic acids.

A number of approaches can be used to detect incorporation of fluorescently-labeled nucleotides into a single nucleic acid molecule. Optical setups include near-field scanning microscopy, far-field confocal microscopy, wide-field epi-illumination, light scattering, dark field microscopy, photoconversion, single and/or multiphoton excitation, spectral wavelength discrimination, fluorophor identification, evanescent wave illumination, and total internal reflection fluorescence (TIRF) microscopy. In general, certain methods involve detection of laser-activated fluorescence using a microscope equipped with a camera. Suitable photon detection systems include, but are not limited to, photodiodes and intensified CCD cameras. For example, an intensified charge couple device (ICCD) camera can be used. The use of an ICCD camera to image individual fluorescent dye molecules in a fluid near a surface provides numerous advantages. For example, with an ICCD optical setup, it is possible to acquire a sequence of images (movies) of fluorophores.

Some embodiments of the present invention use TIRF microscopy for imaging. TIRF microscopy uses totally internally reflected excitation light and is well known in the art. See, e.g., the World Wide Web at nikon-instruments.jp/eng/page/products/tirf.aspx. In certain embodiments, detection is carried out using evanescent wave illumination and total internal reflection fluorescence microscopy. An evanescent light field can be set up at the surface, for example, to image fluorescently-labeled nucleic acid molecules. When a laser beam is totally reflected at the interface between a liquid and a solid substrate (e.g., a glass), the excitation light beam penetrates only a short distance into the liquid. The optical field does not end abruptly at the reflective interface, but its intensity falls off exponentially with distance. This surface electromagnetic field, called the "evanescent wave", can selectively excite fluorescent molecules in the liquid near the interface. The thin evanescent optical field at the interface provides low background and facilitates the detection of single molecules with high signal-to-noise ratio at visible wavelengths.

The evanescent field also can image fluorescently-labeled nucleotides upon their incorporation into the attached template/primer complex in the presence of a polymerase. In one embodiment, imaging is conducted while a labeled nucleotide analog is attached into the template. In other embodiments, imaging is conducted before or after a labeled nucleotide analog is attached to the template. Various combinations of the order of incorporation and imaging may be designed. Total internal reflectance fluorescence microscopy is then used to visualize the attached template/primer duplex and/or the incorporated nucleotides with single molecule resolution.

Analysis

Alignment and/or compilation of sequence results obtained from the image stacks produced as generally described above utilizes look-up tables that take into account possible sequences changes (due, e.g., to errors, mutations, etc.). Essentially, sequencing results obtained as described herein are compared to a look-up type table that contains all possible reference sequences plus 1 or 2 base errors.

EXAMPLES

Provided below is an exemplary synthetic pathway that was used to make Compound 1 (paragraph 18).

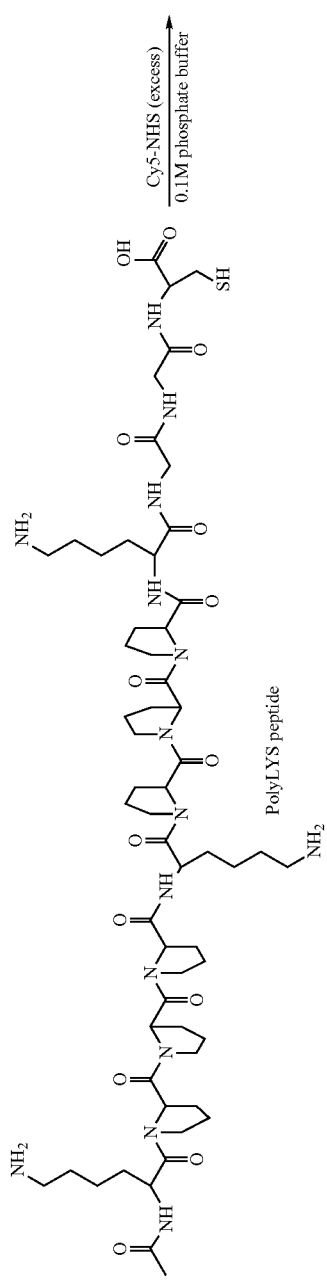

-continued
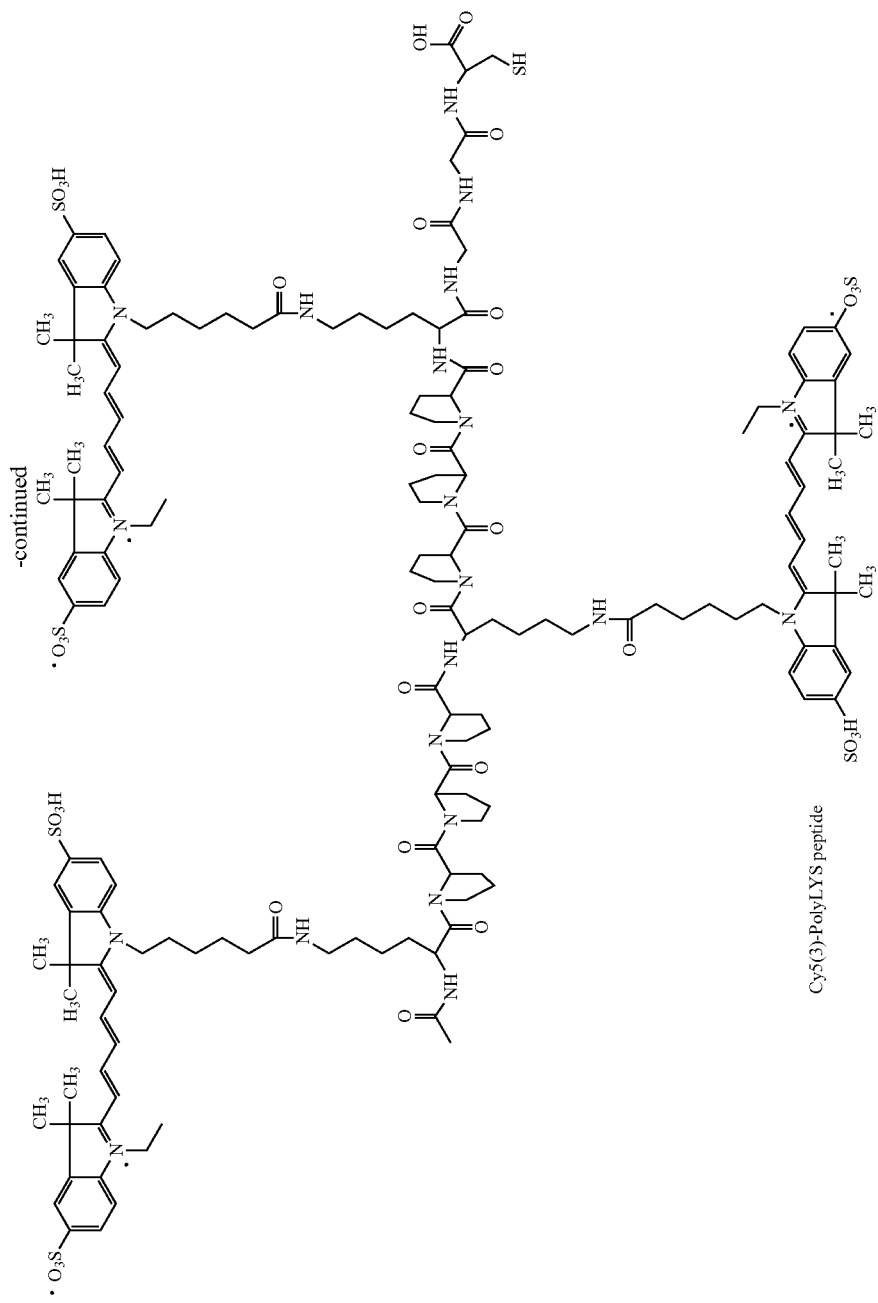
Cy5(3)-PolyLYS peptide

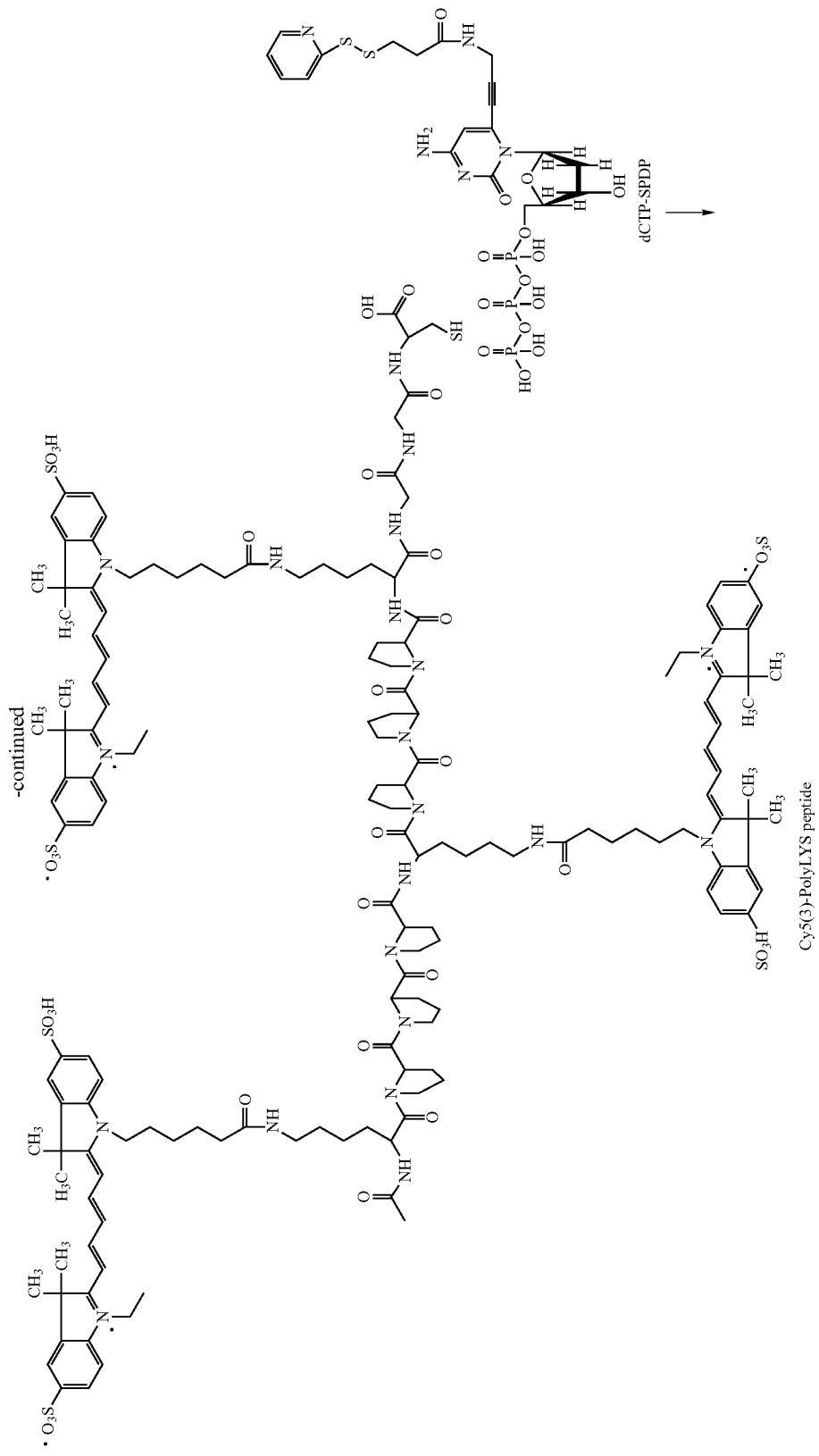

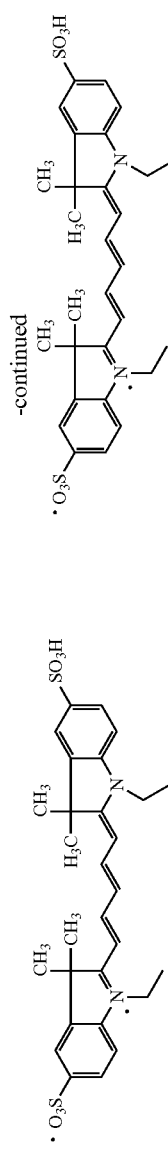
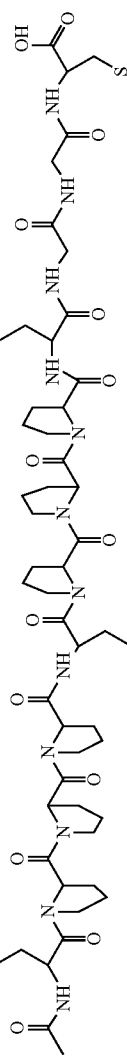
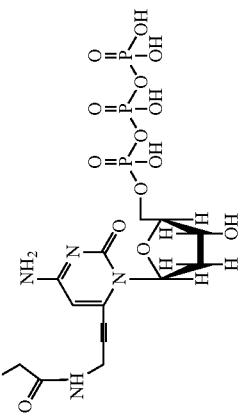
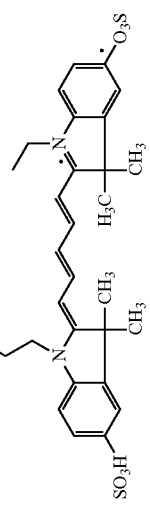
Cy5(3)-PolyLYS peptide

Mitigation of Dye-Dye Quenching

Figure 1B:
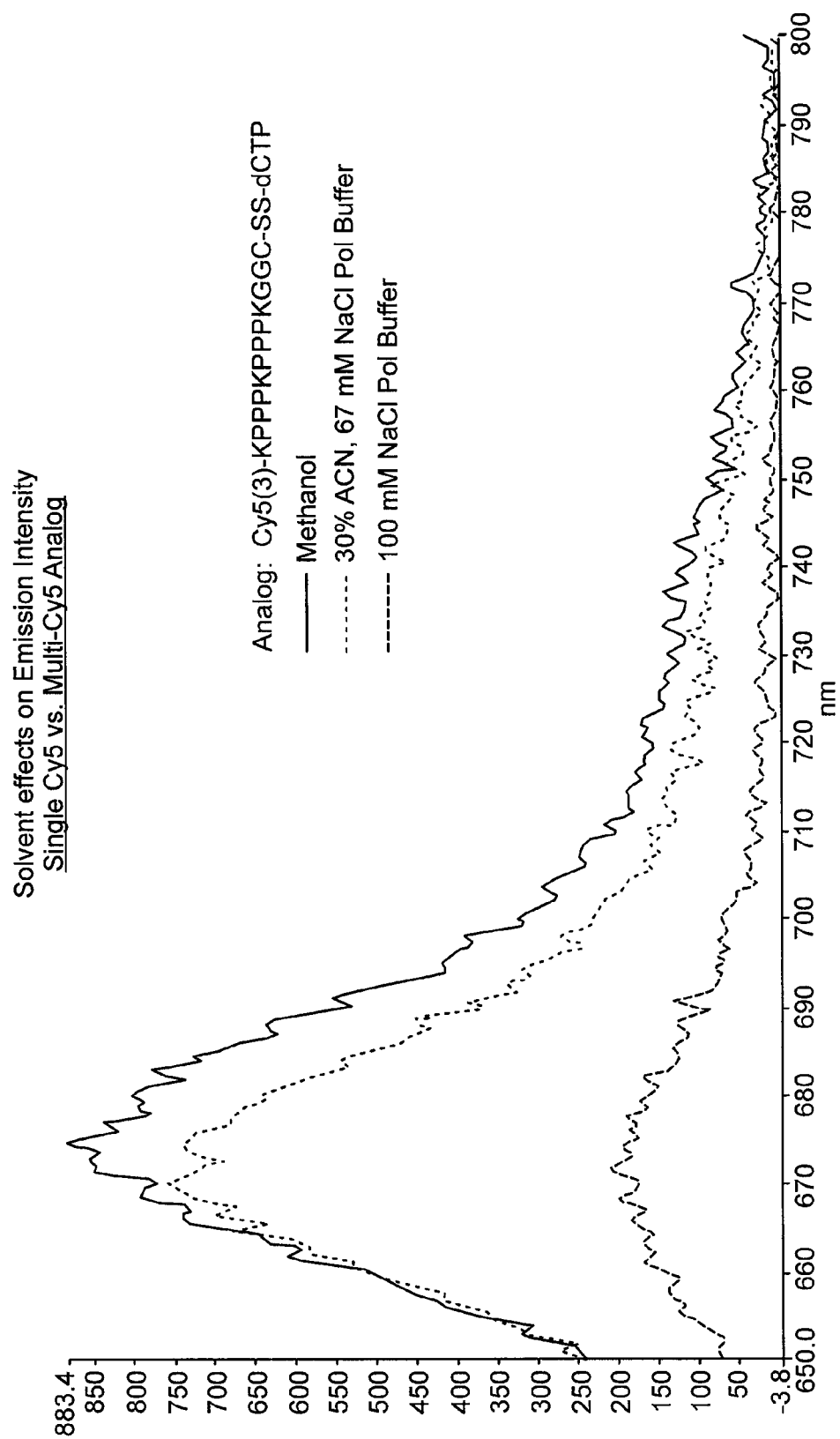

If multiple fluorescent dyes are used, it may be efficacious to minimize any quenching between the dyes by the use of optimal solvent preparations. This is not necessary, but may be useful to improve the resolution of detection. Shown in FIG. 1 are two incorporation experiments under various conditions in which a fluorescently-labeled nucleotide is incorporated into a primer portion of a duplex. In the first panel a single fluor was used (cyanine-5 in this case). Dye intensity in that experiment was not affected by solvent content. In the second panel, multiple Cy-5 dyes were used. As shown in the results, the addition of methanol or acetonitrile to the buffer improved emission intensity over aqueous solution alone.

INCORPORATION BY REFERENCE

All publications, patents, and patent applications cited herein are hereby expressly incorporated by reference in their entirety and for all purposes to the same extent as if each was so individually denoted.

EQUIVALENTS

While specific embodiments of the subject invention have been discussed, the above specification is illustrative and not restrictive. Many variations of the invention will become apparent to those skilled in the art upon review of this specification. Contemplated equivalents of the nucleotide analogs disclosed here include compounds which otherwise correspond thereto, and which have the same general properties thereof, wherein one or more simple variations of substituents or components are made which do not adversely affect the characteristics of the nucleotide analogs of interest. In general, the components of the nucleotide analogs disclosed herein may be prepared by the methods illustrated in the general reaction schema as described herein or by modifications thereof, using readily available starting materials, reagents, and conventional synthesis procedures. The full scope of the invention should be determined by reference to the claims, along with their full scope of equivalents, and the specification, along with such variations.

What is claimed is:

1. A nucleotide analog monomer, wherein the monomer comprises a plurality of detectable labels attached thereto.

2. A nucleotide analog comprising a plurality of detectable labels attached via a cleavable linker to a nitrogenous base portion of said analog.

3. A nucleotide analog monomer, wherein the monomer comprises a sugar, a phosphate, and a nitrogenous base, wherein a plurality of detectable labels are attached at one or more of said sugar, phosphate, and nitrogenous base.

4. The nucleotide analog of claim 3, wherein a first detectable label is attached to said nitrogenous base and a second detectable label is attached to said sugar or said phosphate.

5. The nucleotide analog of claim 3, wherein said plurality of detectable labels is attached to said nitrogenous base.

6. A method for detecting a nucleotide analog of any of claims 1-3, the method comprising imaging the nucleotide analog in the presence of a substance that is capable of disrupting dye:dye interactions thereby resulting in reduced or minimized dye quenching.

7. The method of the claim 6, wherein a water miscible organic solvent is present in an imaging solution used for imaging the nucleotide analog.

8. The method of claim 7, wherein the organic solvent is an alcohol.

9. The method of claim 8, wherein the alcohol is methanol or ethanol.

10. The method of claim 7, wherein the organic solvent is acetonitrile.

11. A method for sequencing a nucleic acid comprising:
directly or indirectly anchoring a nucleic acid duplex to a surface, the duplex comprising a template portion and a primer portion hybridized thereto;
exposing the duplex to nucleotide analog of any one of claims 1-3 or any combination thereof in the presence of a polymerase capable of catalyzing the addition of the nucleotide analog to the primer portion in a template-dependent manner;
detecting incorporation of the nucleotide analog into the primer portion; and
repeating said exposing and detecting steps at least once.

12. The method of claim 11, further comprising:
removing unincorporated nucleotide analog and polymerase in all or some repetitions of the exposing and detecting steps.

13. The method of claim 11, further comprising:
cleaving the label from the nucleotide analog in all or some repetitions of the exposing and detecting steps.

14. A method for sequencing a nucleic acid comprising:
anchoring a nucleic acid duplex to a surface by a polymerase adhered directly or indirectly to the surface, the duplex comprising a template portion and a primer portion hybridized thereto and the polymerase being capable of catalyzing the addition of the nucleotide analog to the primer portion in a template-dependent manner;
exposing the duplex to nucleotide analog of any one of claims 1-3 or any combination thereof in the presence of the polymerase;
detecting incorporation of the nucleotide analog into the primer portion; and
repeating said detecting step at least once.

15. The nucleotide analog according to claim 1, wherein the plurality of detectable labels are all attached at a same attachment site.

16. The nucleotide analog according to claim 1, wherein the plurality of detectable labels are all attached by a same bond.

17. The nucleotide analog according to claim 1, wherein the plurality of detectable labels are all attached via a single cleavable linker.

* * * * *